United States Patent [19]
Finney et al.

[11] 4,066,073
[45] Jan. 3, 1978

[54] COMPOSITE ROD PENILE IMPLANT

[75] Inventors: Roy P. Finney, Tampa, Fla.; Henry Wilfred Lynch, Racine, Wis.

[73] Assignee: Medical Engineering Corporation, Racine, Wis.

[21] Appl. No.: 729,251

[22] Filed: Oct. 4, 1976

[51] Int. Cl.² .............................................. A61F 5/00
[52] U.S. Cl. ......................................................... 128/79
[58] Field of Search ............................... 128/79; 3/1

[56] References Cited

U.S. PATENT DOCUMENTS

| | | | |
|---|---|---|---|
| 3,832,996 | 9/1974 | Kalnbernz | 128/79 |
| 3,893,456 | 7/1975 | Small et al. | 128/79 |
| 3,987,789 | 10/1976 | Timm et al. | 128/79 |
| 3,991,752 | 11/1976 | Gerow | 128/79 |

*Primary Examiner*—Lawrence W. Trapp
*Attorney, Agent, or Firm*—Andrus, Sceales, Starke & Sawall

[57] ABSTRACT

A penile implant provides a desirable erectness to the penis while at the same time permitting the penis to assume a flaccid position. The implant comprises an elongated rod formed of silicone rubber or other suitable material positionable within the corpus cavernosum of the penis. The rod has axially arrayed sections of various flexural properties. A proximal section suitable for positioning adjacent the pubis is medium stiff in flexure. A longer distal section located in the pendulus penis may be medium stiff or stiffer in flexure. The distal and proximal sections are separated by a very flexible hinge section.

23 Claims, 6 Drawing Figures

U.S. Patent  Jan. 3, 1978  4,066,073
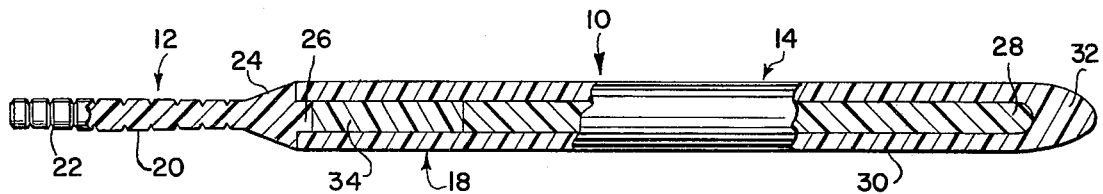
Fig. 1
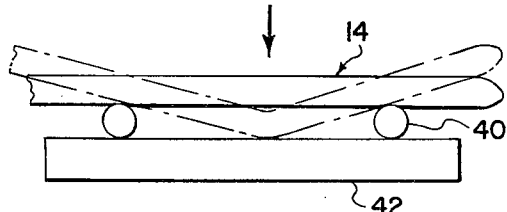
Fig. 4
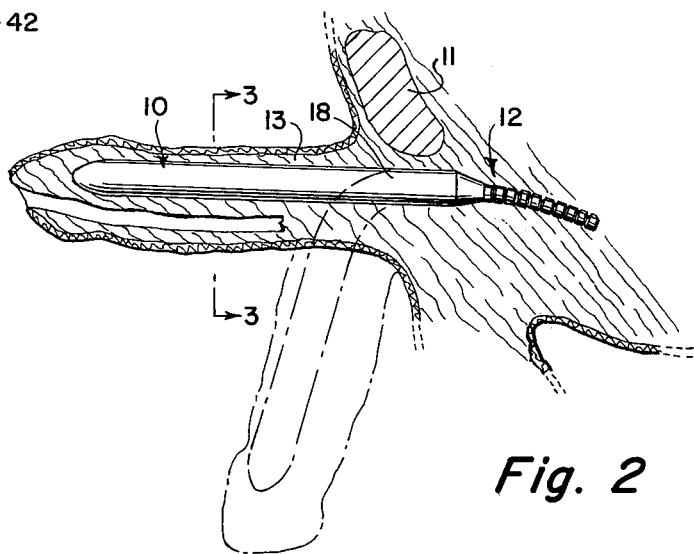
Fig. 2
Fig. 3
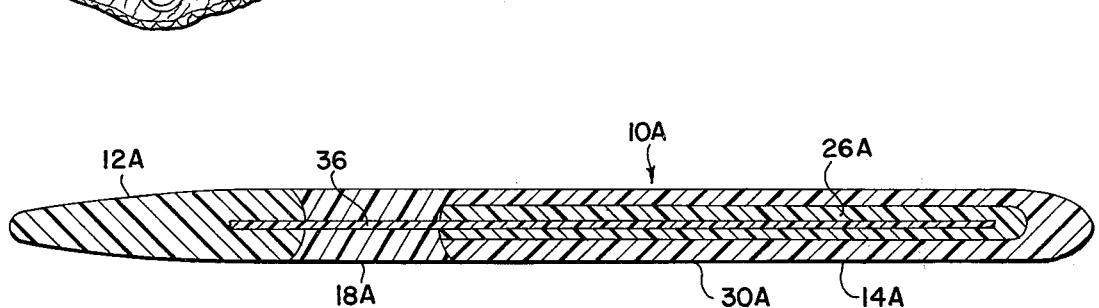
Fig. 5
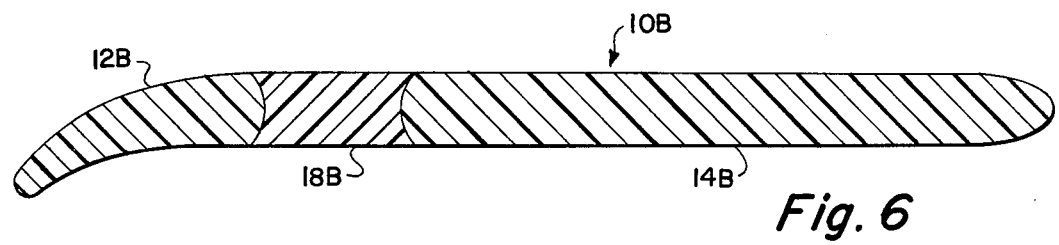
Fig. 6

COMPOSITE ROD PENILE IMPLANT

BACKGROUND OF THE INVENTION

1. Field of the Invention

The present invention relates to a penile implant.

2. Description of the Prior Art

It is known to use implants to provide stiffness to the penis. The pertinent anatomy suggests the use of a rod of suitable stiffness insertable in the penis to provide the desired properties. However, the stiffness becomes permanent, requiring the wearing of special underwear to disguise the stiffness.

This drawback has led to the development of rodlike implants in which the stiffness of the rod is reduced along a major portion of its length. See, for example, U.S. Pat. No. 3,893,456 to Small, et al which discloses a hollow rod filled with foam. However, the flexure of such an implant must be a compromise between the stiffness and limpness desired, with the result that neither property is completely satisfactory. A large number of such devices must be available to accommodate the anatomical size ranges likely to be encountered.

SUMMARY OF THE PRESENT INVENTION

The present invention contemplates a rod-like penile implant having a pair of stiff portions separated from each other by a soft hinge portion. A short proximal portion is positioned inside the corpus cavernosum adjacent the pubis for supporting the implant. A longer distal portion is insertable in the corpus cavernosum of the pendulus penis. Preferably the distal portion is stiff while the proximal protion is of lesser, medium stiffness. A very flexible hinge portion separates the two. The stiff proximal and distal portions provide desired stiffness to the penis while the hinge portion permits it to be conveniently and easily bent.

BRIEF DESCRIPTION OF THE DRAWING

FIG. 1 is a partially cross sectional view of a preferred embodiment of the penile implant of the present invention.

FIG. 2 shows generally the positioning of the implant within the penis and pubic area.

FIG. 3 is a cross sectional view taken along the line 3—3 of FIG. 2.

FIG. 4 is a diagram of a device for measuring the stiffness of the distal portion of the implant.

FIG. 5 is a cross sectional view of another embodiment of the penile implant according to the present invention.

FIG. 6 is a cross sectional view of a simple embodiment of the penile implant of the present invention.

DESCRIPTION OF THE PREFERRED EMBODIMENT

The penile implant of the present invention is identified by the numeral 10 in FIG. 1. Implant 10 includes short proximal portion 12 which lies within the crus of the corpus cavernosum when implant 10 is implanted. Implant 10 also includes longer distal portion 14 which is located within the corpus cavernosum 16 of the pendulus penis when the implant is in position, as shown in FIGS. 2 and 3. Intermediate hinge portion 18 is located between proximal portion 12 and distal portion 14 and generally below the pubis when the implant is implanted. Implant 10 and its various parts are typically circular in cross section but may be of oval or other appropriate configuration. As shown in FIG. 3, implant 10 is usually implanted in pairs.

Penile implant 10 may be formed of a physiologically inert material such as medical grade, silicone rubber. The stiffness of the rubber may be controlled by the type and amount of catalyst used to cure the elastomer and the amount of heat and time employed during the curing or vulcanizing process.

While the term "stiff", is used in this specification and in the claims, as a convenient and generally understood description of the desired physical properties of implant 10 and its various portions, a more precise, technical term is flexural modulus; that is, the ratio of applied force to resulting deflection. However, most tables of properties do not describe the stiffness properties or the flexural modulus for rubber or rubber-like materials. Rather they list related properties, such as hardness and tensile strength. These qualities are, therefore, used in the following description.

Hardness may be measured by a durometer, such as a Shore A durometer which ascertains the depth of penetration of a specified indentor into a specimen under specified conditions. A scale is chosen so that zero represents a material showing no measurable resistance to indentation and 100 represents a material showing no measurable indentation.

Tensile strength is the unit stress which produces failure of a specimen in tension. A Scott Tensile Tester may be used for this purpose.

Proximal portion 12 of implant 10 is approximately 8 cm in length. The major length of portion 12 is a rod 20 approximately 8 mm in diameter. Rod 20 may contain axially spaced grooves 22 which assist in trimming proximal portion 12 to the correct length during surgery. A truncated conical section 24 increases the diameter of proximal portion 12 from that of rod 20 to the diameter of hinge portion 18 and distal portion 14 which are approximately 12 mm in diameter. Stub 26 assists in the joinder of proximal portion 12 to the remaining portions of implant 10. Proximal portion 12 may be formed of a silicone rubber having a medium stiffness, for example, a Shore A hardness of 55 ± 5 and a minimum tensile strength of 1000 psi.

Distal portion 14 contains an inner core 28. Inner core 28 may be formed of material as stiff or stiffer than proximal portion 12. For example, material having a Shore A hardness of 70 or higher may be used. The diameter of core 28 may be 9 mm. Core 28 is covered with an outer sheath 30 of very soft material which produces a natural feel and helps protect the overlying tissues from damage which might occur from external trauma. Sheath 30 enlarges the diameter of distal portion 14 to approximately 12 mm. The length of distal portion 14 varies with the patient, lengths in a range of 6 to 12 cm being typical. The sheath also includes distal tip 32 which is typically paraboloidal in shape to enhance the physiological compatibility of implant 10. By increasing the stiffness of core 28 its diameter may be decreased, permitting the thickness of sheath 30 to be increased, improving the natural feel of the implant. Because of the covering provided by sheath 30, a stiffer plastic material other than silicone rubber, such as polyethylene, may be used for core 28 if desired.

Sheath 28 extends over central portion 34 of very soft material having properties similar to sheath 30 to form hinge section 18.

The rubber of sheath 28 and central portion 34 may have a Shore A hardness of, for example, 20. The softness of this material and the small size of central portion 34 prevents the development of meaningful tensile strength figures. Rather, the tensile modulus at 100 percent elongation for solid rod of the material of hinge 18, 12 mm in diameter may be examined. A desirable modulus is 20 to 30 psi. Hinge portion 18 is approximately 4 cm long. Sheath 28 also extends over stub 26 of proximal portion 12.

While the physical properties of the various portions of implant 10 have been described in detail above, the major requirement of implant 10 is that it reproduce the natural physiology of the penis. The following test has been devised to measure and compare the stiffness of, particularly, the composite, distal portion 14 of implant 10. Distal portion 14 is placed across two supports 40 3/16th inch high, spaced 2½ inches apart on a plate 42, as shown in FIG. 4. Force is then applied to the upper surface of distal portion 14 midway between supports 40. The force required to bend the distal portion 14 until it touches surface plate 42 becomes a measure of the stiffness of distal portion 14. A stiffness of distal portion 14 which requires between 225 and 430 grams force for the above deflection has been found suitable for implant 10. A stiffness requiring a deflection force of 340 grams is presently deemed preferred.

To form penile implant 10, sheath 30 is molded of the soft material. As noted supra, sheath 30 is closed at one end and shaped to fit the end of the corpus cavernosum. The open end of sheath 30 may be trimmed to vary the length of distal portion 14 of implant 10. Core 28, formed by molding or extrusion, is trimmed in accordance with the length of the distal portion of the implant being produced, inserted, and cemented in the interior of sheath 30. Central portion 34 of the soft bendable material of hinge section 18 is then inserted and cemented in the remaining length of sheath 28. Central portion 34 is typically molded.

Proximal portion 12 is also typically molded because of its shape. Stub 26 is cemented in sheath 30. Preferably, assembled implant 10 is dip coated in a dispersion of silicone rubber to give it a smooth, attractive finish.

The preferred method of implanation of implant 10 is through the perineum. After appropriate incision, the corpus cavernosum is dilated distally and proximally to accept the implant. The appropriate anatomical measurements are made to insure that the hinged portion 18 of implant 10 will be positioned at the base of the penis below the pelvic bone. An implant having an appropriately sized distal portion 14 is obtained and the distal portion inserted into the corpus cavernosum of the penis. The proximal portion 12 of implant 10 is cut to the appropriate length. During the manufacture of implant 10 the length of proximal portion 12 is deliberately made longer than necessary thereby permitting it to be trimmed to the correct length at the time of surgery. Only one implant of each distal portion length need, therefore, be available since other anatomical size variations may be accommodated by trimming proximal portion 12. This greatly reduces the number of implant sizes which must be produced over that which would be required if no such size alteration were possible.

Proximal portion 12 is inserted in the dilated crus after trimming. The incision is then closed. The identical procedure is formed on the other side of the penis to complete the surgical procedure. Distal portions 14 of the two implants may diverge laterally at hinge portions 18 to accommodate the anatomy and provide lateral stability to the penis.

FIG. 5 shows another embodiment 10A of the penile implant of the present invention. The diameter of implant 10A of FIG. 2 is generally uniform along its length. The proximal portion 12A is tapered at its end. Sheath 30A covers only distal portion 14A and the diameter of hinge portion 18A equals that of the other portions of the implant. The transverse surfaces of hinge portion 18A may be concave to accommodate the convex ends of proximal portion 12A and distal portion 14A, a configuration which aids in the hinging action of the implant. Cord 36 extends from proximal portion 12A through hinge 18A to core 26A of distal portion 14A to reinforce the implant.

In the embodiment 10B shown in FIG. 6, the core 28 is omitted. Proximal portion 12B and distal portion 14B may be formed of medium stiff silicone rubber while hinge portion 18B is formed of extra soft silicone rubber.

Various modes of carrying out the invention are contemplated as being within the scope of the following claims particularly pointing out and distinctly claiming the subject matter which is regarded as the invention.

We claim:

1. An elongated, rod-like, penile implant comprising, in a generally axial orientation:
   a relatively stiff proximal portion receivable in the crus of the corpus cavernosum for supporting the implant;
   a relatively stiff distal portion suitable for positioning, in the corpus cavernosum of the pendulus penis; and
   a relatively flexible hinge portion intermediate said proximal and distal portions.

2. The implant according to claim 1 wherein the stiffness of the proximal portion and the distal portion are the same.

3. The implant according to claim 1 wherein the stiffness of the distal portion is greater than that of the proximal portion.

4. The implant according to claim 1 wherein the hardness of the material forming the proximal portion is approximately 55 as measured by a Shore A durometer.

5. The implant according to claim 4 wherein the material forming the proximal portion has a minimum tensile strength of 1000 psi.

6. The implant according to claim 1 wherein the hardness of the material forming the hinge portion is approximately 20 as measured by a Shore A durometer.

7. The implant according to claim 1 wherein the stiffness of said distal portion is such as to require a centrally applied force of between 225 and 430 grams to deflect said portion 3/16th inch when spanning a distance of 2½ inches.

8. The implant according to claim 7 wherein the stiffness of said distal portion is such as to require a centrally applied force of 340 grams to deflect said portion 3/6th inch when spanding a distance of 2½ inches.

9. The implant according to claim 1 wherein said distal portion comprises a relatively stiff core covered with a soft, flexible sheath.

10. The implant according to claim 9 wherein the hardness of the material forming said core of said distal portion is approximately 70 or more as measured by a Shore A durometer.

11. The implant according to claim 9 wherein said hinge portion is formed of the same material as said sheath.

12. The implant according to claim 11 wherein said hinge portion includes a central portion covered by said sheath.

13. The implant according to claim 12 wherein the portions of said implant are cemented together.

14. The implant according to claim 1 wherein a cord-like reinforcing means extends along the axis of said implant from said proximal portion through said hinge portion to said distal portion.

15. The implant according to claim 9 wherein said sheath includes a closed tip.

16. The implant according to claim 1 wherein said proximal portion includes a rod-like section having a diameter less than the remainder of the implant and a sloping portion joined to said hinge portion.

17. The implant according to claim 15 wherein the rod-like section of said proximal portion contains a plurality of circumferential grooves.

18. The implant according to claim 1 wherein said distal portion is of predetermined length.

19. The implant according to claim 1 wherein the length of said proximal portion is such as to permit trimming for altering the length of the implant to accommodate the anatomy of the patient.

20. The implant according to claim 1 wherein said portions are cemented together.

21. The implant according to claim 9 wherein the portions of said implant are cemented together.

22. The implant according to claim 1 wherein said implant includes an exterior coating over said portions.

23. The implant according to claim 22 wherein said implant includes an exterior coating of silicone rubber.

* * * * *